(12) United States Patent
Campbell et al.

(10) Patent No.: US 10,731,079 B2
(45) Date of Patent: *Aug. 4, 2020

(54) FLAME RETARDANT POLYCAPROLACTONE

(71) Applicant: International Business Machines Corporation, Armonk, NY (US)

(72) Inventors: Eric J. Campbell, Rochester, MN (US); Sarah K. Czaplewski, Rochester, MN (US); Brandon M. Kobilka, Tucson, AZ (US); Jason T. Wertz, Pleasant Valley, NY (US)

(73) Assignee: International Business Machines Corporation, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/393,499

(22) Filed: Apr. 24, 2019

(65) Prior Publication Data

US 2019/0249086 A1     Aug. 15, 2019

Related U.S. Application Data

(62) Division of application No. 15/589,998, filed on May 8, 2017, now Pat. No. 10,308,875.

(51) Int. Cl.
| | | |
|---|---|---|
| *C09K 21/12* | (2006.01) | |
| *C07D 313/02* | (2006.01) | |
| *C08K 5/02* | (2006.01) | |
| *C08K 5/04* | (2006.01) | |
| *C09K 21/14* | (2006.01) | |
| *C07D 313/04* | (2006.01) | |
| *C07F 9/655* | (2006.01) | |
| *C07F 9/09* | (2006.01) | |
| *C08G 63/682* | (2006.01) | |
| *C08G 63/692* | (2006.01) | |
| *C08F 4/16* | (2006.01) | |
| *C08G 63/08* | (2006.01) | |

(52) U.S. Cl.
CPC .......... *C09K 21/12* (2013.01); *C07D 313/02* (2013.01); *C07D 313/04* (2013.01); *C07F 9/091* (2013.01); *C07F 9/093* (2013.01); *C07F 9/65525* (2013.01); *C08F 4/16* (2013.01); *C08G 63/08* (2013.01); *C08G 63/6822* (2013.01); *C08G 63/6922* (2013.01); *C08K 5/02* (2013.01); *C08K 5/04* (2013.01); *C09K 21/14* (2013.01)

(58) Field of Classification Search
CPC ........ C09K 21/12; C09K 21/14; C08G 63/08; C07D 313/04; C07D 313/02; C07F 9/091; C07F 9/65525; C07F 9/093; C08K 5/04; C08K 5/02
USPC .......................................................... 524/7
See application file for complete search history.

(56) References Cited

U.S. PATENT DOCUMENTS

| | | |
|---|---|---|
| 8,592,539 B2 | 11/2013 | Tang et al. |
| 9,187,597 B1 | 11/2015 | Boday et al. |
| 2002/0155092 A1 | 10/2002 | Leong et al. |
| 2007/0066748 A1 | 3/2007 | Lewandowski et al. |
| 2016/0046761 A1 | 2/2016 | Hegmann et al. |
| 2017/0029616 A1 | 2/2017 | Boday et al. |

FOREIGN PATENT DOCUMENTS

EP       1188761 A1 *  3/2002  .......... C01B 15/037

OTHER PUBLICATIONS

Park et al., J. Coatings Technology, 71, 899, 59-65, 1999. (Year: 1999).*
Kroner et al., "The Gas-Phase Acidity of 2(3H)-Oxepinone: A Step toward an Experimental Heat of Formation for the 2-Oxepinoxy Radical," Journal of the American Chemical Society, 2005, vol. 127, No. 20, pp. 7466-7473. DOI: 10.1021/0050173u.
Lou et al., "Living Ring-Opening (Co)polymerization of 6,7-Dihydro-2(5H)-oxepinone into Unsaturated Aliphatic Polyesters," Macromolecules 2001, 34, pp. 5806-5811.
Park et al., "Preparation and Physical Properties of Polyurethane Flame Retardant Coatings Using Phosphorus-Containing Lactone Modified Polyesters," Journal of Coatings Technology, Dec. 1999, vol. 71, No. 899, pp. 59-65. DOI: 10.1007/BF02697979.
Zhang et al., "Synthesis of well-defined carboxyl poly(ε-caprolactone) by fine-tuning the protection group," Polymer Chemistry, 2016, 9 pages, The Royal Society of Chemistry. DOI: 10.1039/c6py00932h.
Gilman, J., "Chapter 3: Flame Retardant Mechanism of Polymer-Clay Nanocomposites," Flame Retardant Polymer Nanocomposites, Section 3.1.1, pp. 68-69, 2007, John Wiley & Sons, Inc. (Eds. Morgan et al.) https://books.google.com/books?id=LAmOb4p8lwlC&pg=PA68&lpg=PA68&dq=polycaprolactone+flame+retardant&source=bl&ots=iWPMcOmfZB&sig=UZhr1GP0I_OMPXVCRc9vSo7LhGg&hl=en&sa=X&ved=0ahUKEwie1tiP_6PQAhXCLSYKHXWkAyEQ6AEITjAE#v=onepage&q=polycaprolactone%20flame%20retardant&f=false.
STIC Search—Feb. 3, 2019 (Year: 2019) from U.S. Appl. No. 15/480,785, filed Nov. 1, 2017, 48 pages.

(Continued)

*Primary Examiner* — Hui H Chin
(74) *Attorney, Agent, or Firm* — Kelsey M. Skodje (57) ABSTRACT

A process for forming a flame retardant polymer, as well as the flame retardant polymer, are disclosed. A flame retardant polymer is a polymer that can be resistant to thermal degradation and/or thermal oxidation. A flame retardant polymer can be mixed or otherwise incorporated into a standard polymer to give flame retardancy to the standard polymer. The flame retardant polymers can include polycaprolactone functionalized with flame retardant substituents. The flame retardant substituents can include halides, substituted phosphoryl, and substituted phosphonyl.

6 Claims, 3 Drawing Sheets

(56) References Cited

OTHER PUBLICATIONS

Campbell et al., "Flame Retardant Polycaprolactone," U.S. Appl. No. 15/589,998, filed May 8, 2017.
Campbell et al., "Phosphorus-Containing Caprolactone Monomers for Synthesis of Flame Retardant Polycaprolactones," U.S. Appl. No. 15/480,785, filed Apr. 6, 2017.
Campbell et al., "Phosphorus-Containing Caprolactone Monomers for Synthesis of Flame Retardant Polycaprolactones," U.S. Appl. No. 16/393,568, filed Apr. 24, 2019.
List of IBM Patents or Patent Applications Treated as Related, Signed Apr. 24, 2019, 2 pages.
Campbell et al., "Phosphorus-Containing Caprolactone Monomers for Synthesis of Flame Retardant Polycaprolactones," U.S. Appl. No. 16/574,866, filed Sep. 18, 2019.
List of IBM Patents or Patent Applications Treated as Related, Signed Sep. 18, 2019, 2 pages.

* cited by examiner

FLAME RETARDANT POLYCAPROLACTONE

BACKGROUND

There is considerable interest in the use of renewably-sourced polymers for electronic applications. Polycaprolactone (PCL) is a commercially available, renewably-sourced polymer that has been successfully blended with various polymers as an impact modifier to improve toughness, resulting in blends with a sizeable fraction of bio-based material. PCL is also used as a building block for the manufacturing of polyurethanes.

SUMMARY

Some embodiments discussed herein are related to flame retardant polymers. A flame retardant polymer is a polymer that can be resistant to thermal degradation and/or thermal oxidation. A flame retardant polymer can be mixed or otherwise incorporated into a standard polymer to give flame retardancy to the standard polymer.

The compounds described herein may be used in flame retardant polymers.

Some embodiments include a process of forming a flame retardant polycaprolactone, the process comprising utilizing a caprolactone molecule to form a hydroxyl-functionalized caprolactone molecule, chemically reacting the hydroxyl-functionalized caprolactone molecule with a phosphorus-based compound to form a caprolactone monomer having phosphorus-based moieties, polymerizing a mixture that includes at least the caprolactone monomer to form a flame retardant polycaprolactone.

Some embodiments include a flame retardant compound represented by a formula:

wherein $R^1$, $R^2$, $R^3$, $R^4$, and $R^5$ are independently selected from H, F, Cl, Br, and I.

Some embodiments include a compound represented by a formula:

—O—FR wherein FR is selected from optionally substituted phosphoryl and optionally substituted phosphonyl.

Some embodiments include a polymer that includes the monomer represented by a formula.

wherein $R^1$, $R^2$, $R^3$, $R^4$, and $R^5$ are each independently selected from H, F, Cl, Br, I, and —O—FR.

Some embodiments include a polymer represented by a formula.

wherein $R^1$, $R^2$, $R^3$, $R^4$, and $R^5$ are independently selected from H, F, Cl, Br, and I, and wherein a relative percentage of n block to m block is between 2% and 20%.

DETAILED DESCRIPTION

Bio-based compounds are increasingly being used in the syntheses of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale. Examples of these strategies include plant-based or microorganism-based approaches. Plant-based approaches can involve obtaining a material directly from a plant or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Examples of uses for bio-based compounds include polymers, flame retardants, cross-linkers, etc. In some examples, bio-based polymers and petroleum-based polymers are blended to form a polymer composite. However, polymers can also be entirely bio-based, or produced from a combination of bio- and petroleum-based monomers. Bio-based compounds can impart flame-retardant properties to bio- and petroleum-based polymers. For example, flame-retardant monomers or cross-linkers can be incorporated into polymers. Additionally, flame-retardant small molecules can be blended with the polymers.

In some embodiments, polymers can be heteropolymers consisting of 2 or more different monomers. In some embodiments, polymers can be homopolymers consisting of only one monomer. For example, in one embodiment a polymer can be a heteropolymer of unsubstituted caprolactone and substituted caprolactone. In another embodiment, the polymer can be a homopolymer of only substituted caprolactone.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-5 or 0-2 carbon atoms; and 0-5 or 0-3 heteroatoms, wherein each heteroatom may independently be: N, O, S, Si, F, Cl, Br, or I; provided that the substituent includes at least one C, N, O, S, Si, F, Cl, Br, or I atom. In other embodiments, examples of substituents can include, but are not limited to, optionally substituted alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, O-phenyl, N-thiocarbamyl, C-amido, N-amido, S-sulfonamido, N-sulfonamido, isocyanato, thiocyanato, isothiocyanato, nitro, phosphoryl, phosphonyl, silyl, sulfenyl, sulfinyl, sulfonyl, haloalkyl, haloalkoxyl, trihalomethanesulfonyl, trihalomethanesulfonamido, amino, etc. Wherever a substituent is described as "optionally substituted," that substituent can be substituted with the above substituents. In some embodiments, when a substituent is phosphorus-based, the substituent should be understood to include a phosphate, phosphonate, phosphoryl, or phosphonyl moiety.

"Aryl" refers to an aromatic substituent that may be a single ring or multiple rings. The aromatic rings of the aryl group may each and optionally contain heteroatoms, for example, as in phenyl, pyridine, pyrazine, pyrimidine, carbazolyl, or imidazole. The aryl group can be optionally substituted with one or more aryl group substituents which can be the same or different, where "aryl group substituent" includes alkyl, aryl, arylalkyl, hydroxy, alkoxyl, aryloxy, arylalkoxyl, carboxy, —CN, acyl, halo, nitro, alkoxycarbonyl, aryloxycarbonyl, arylalkoxycarbonyl, acyloxyl, acylamino, aroylamino, carbamoyl, alkylhalide, alkylcarbamoyl, dialkylcarbamoyl, arylthio, alkylthio, alkylene, boronic acid, and —NRR', where R and R' can be each independently hydrogen, alkyl, aryl, -aryl-alkyl, and -alkyl-aryl.

In some embodiments, the number of carbon atoms in an alkyl substituent or moiety can be specified herein. For example, a substituent described as "optionally substituted $C_{1-6}$ alkyl" should be understood to be an alkyl base moiety that has between one and six carbons that can be optionally substituted with substituents as described above.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by or -, attachment may occur at any position normally occupied by a hydrogen atom. For example, attachment would occur at the in the caprolactone        polycaprolactone

Some embodiments include a compound of any of the following formulas:

(Formula A)

(Formula B)

(Formula 1)

(Formula 2)

wherein $R^1$, $R^2$, $R^3$, $R^4$, and $R^5$ can independently be selected from H, F, Cl, Br, I, OH, optionally substituted $C_{1-6}$ alkyl, optionally substituted phosphoryl, or optionally substituted phosphonyl and wherein a relative percentage of n block to m block can be between 2% and 20%, wherein FR is and wherein $R^8$ and $R^9$ are selected from H, aryl, optionally substituted phenyl, or optionally substituted $C_{1-6}$ alkyl.

With respect to any relevant formula or structural representation herein, such as Formulas A, 1, and 2, $R^1$ can be H or any substituent such as F, Cl, Br, I, OH, optionally substituted $C_{1-3}$ alkyl, optionally substituted —OR, optionally substituted phosphoryl, optionally substituted phosphonyl, or —O—FR (Formula B). In some embodiments, $R^1$ is Br. In some embodiments, $R^1$ is H. In some embodiments $R^1$ is optionally substituted phosphoryl. In some embodiments, $R^1$ is —O—FR.

With respect to any relevant formula or structural representation herein, such as Formula A, B, 1, and 2, FR can be optionally substituted phosphoryl or optionally substituted phosphonyl. For example, —O—FR as described in Formula 2 can be —O-phosphoryl or —O-phosphonyl, either being optionally substituted. In some embodiments, FR is wherein $R^8$ and $R^9$ are selected from H, aryl, optionally substituted phenyl, or optionally substituted $C_{1-6}$ alkyl. In some embodiments, FR is wherein $R^8$ and $R^9$ are selected from H, aryl, optionally substituted phenyl, or optionally substituted $C_{1-6}$ alkyl.

With respect to any relevant formula or structural representation herein, such as Formulas A, 1, and 2, $R^2$ can be H or any substituent such as F, Cl, Br, I, OH, optionally substituted $C_{1-3}$ alkyl, optionally substituted —OR, optionally substituted phosphoryl, optionally substituted phosphonyl, or —O—FR. In some embodiments, $R^2$ is Br. In some embodiments, $R^2$ is H. In some embodiments $R^2$ is optionally substituted phosphoryl. In some embodiments, $R^2$ is —O—FR.

With respect to any relevant formula or structural representation herein, such as Formulas A, 1, and 2, $R^3$ can be H or any substituent such as F, Cl, Br, I, OH, optionally substituted $C_{1-3}$ alkyl, optionally substituted —OR, optionally substituted phosphoryl, optionally substituted phosphonyl, or —O—FR. In some embodiments, $R^3$ is Br. In some embodiments, $R^3$ is H. In some embodiments $R^3$ is optionally substituted phosphoryl. In some embodiments, $R^3$ is —O—FR.

With respect to any relevant formula or structural representation herein, such as Formulas A, 1, and 2, $R^4$ can be H or any substituent such as F, Cl, Br, I, OH, optionally substituted $C_{1-3}$ alkyl, optionally substituted —OR, optionally substituted phosphoryl, optionally substituted phosphonyl, or —O—FR. In some embodiments, $R^4$ is Br. In some embodiments, $R^4$ is H. In some embodiments $R^4$ is optionally substituted phosphoryl. In some embodiments, $R^4$ is —O—FR.

With respect to any relevant formula or structural representation herein, such as Formulas A, 1, and 2, $R^5$ can be H or any substituent such as F, Cl, Br, I, OH, optionally substituted $C_{1-3}$ alkyl, optionally substituted —OR, optionally substituted phosphoryl, or optionally substituted phosphonyl. In some embodiments, $R^5$ is Br. In some embodiments, $R^5$ is H. In some embodiments $R^5$ is optionally substituted phosphoryl. In some embodiments, $R^5$ is —O—FR.

With respect to any relevant formula or structural representation herein, such as Formulas A, B, 1, and 2, $R^8$ can be H, optionally substituted aryl, optionally substituted phenyl, or optionally substituted $C_{1-6}$ alkyl. In some embodiments, $R^8$ is optionally substituted phenyl. In some embodiments, $R^8$ is optionally substituted $C_{1-6}$ alkyl.

With respect to any relevant formula or structural representation herein, such as Formulas A, B, 1, and 2, $R^9$ can be H, optionally substituted aryl, optionally substituted phenyl, or optionally substituted $C_{1-6}$ alkyl. In some embodiments, $R^9$ is optionally substituted phenyl. In some embodiments, $R^9$ is optionally substituted $C_{1-6}$ alkyl.

Polymers as disclosed herein can also include one or more other polymers. Examples of polymers can include epoxy, a polyhydroxyurethane, a polycarbonate, a polyester, a polyacrylate, a polyimide, a polyamide, a polyurea, a poly(vinylester), etc. Combinations of polymers can include chemical crosslinking, mixing, blending, forming a matrix, a composite of different polymers, etc. In some embodiments, the copolymer or monomer ratio can be used to control the properties of a product polymer. In some embodiments, the percentage by mass of substituted monomer in a polymer can be from about 1% to about 30%, for example from about 5% to about 20%, or any other percentage bound therein. In some embodiments, the ratio of substituted monomer to unsubstituted monomer in a polymer can be a ratio of between 1:30 to about 1:4, such as about 1:20 to about 1:5, or any other ratio bound therein. For example, a precursor copolymer ratio of 1:10 (substituted to unsubstituted monomers) before polymerization would result in a polymer that has a 1:10 ratio of substituted to unsubstituted monomers. In some embodiments, a polymer with a 1:10 copolymer ratio can have different properties than a polymer with a 1:20 copolymer ratio.

In some embodiments, the polymers disclosed herein can be used as single component materials, part of blended polymeric materials, or as components of composite materials. In some embodiments, the polymers disclosed herein can be added to other materials to add to the flame retardancy characteristics of the material being modified. In some embodiments, multiple flame retardant monomers can be blended with an unsubstituted monomer to form a final polymer. In some embodiments, blending is done after polymerization.

A flame retardant polymer is a polymer that can be resistant to thermal degradation and/or thermal oxidation. In some embodiments, a flame retardant polymer can be mixed with another polymer to form a polymer matrix composite. For example, the flame retardant polymer can be otherwise incorporated into a standard polymer to give flame retardancy to the standard polymer.

One example of a polymer that can be made flame-retardant by the addition of flame-retardant polymers as disclosed herein is polycarbonate-acrylonitrile butadiene styrene (PC-ABS), a plastic that is often used in electronics hardware. The flame retardant polymers disclosed herein can also be incorporated into polyurethane. Polyurethane is a versatile polymer used in applications that include acoustic dampening, cushioning, plastics, synthetic fibers, insulation, adhesives, etc. The polymers disclosed herein can also be added to adhesives such as bio-adhesives, elastomers, thermoplastics, emulsions, thermosets, etc. Further, materials containing the polymers disclosed herein can be incorporated into various devices with electronic components that can include printed circuit boards (PCBs), semiconductors, transistors, optoelectronics, capacitors, resistors, etc.

In another example, the process of forming a flame retardant polycaprolactone can include utilizing a caprolactone molecule to form a hydroxyl-functionalized caprolactone molecule. Then following the formation of the hydroxyl-functionalized caprolactone molecule, chemically reacting the hydroxyl-functionalized caprolactone molecule with a halide to form a halogen-functionalized caprolactone monomer. Following the formation of the monomer, polymerizing a mixture that includes at least the halogen-functionalized caprolactone monomer to form a flame retardant polycaprolactone Resins for printed circuit boards (PCBs) can be made flame-retardant by incorporating flame retardant polymers as disclosed herein. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polycarbonate, a polyester, a polyacrylate, a polyimide, a polyamide, a polyurea, a poly(vinyl-ester), etc. Flame-retardant polymers as disclosed herein can be added to the resin in order to prevent the PCB from catching fire when exposed to high temperature environments or electrical power overloads. In some embodiments, flame retardant polymers as disclosed herein, when added to other materials as explained above, can add to the self-extinguishing characteristics of materials that have been exposed to an open flame. For example, any article of manufacture or composition can have incorporated therein a flame retardant compound as disclosed herein.

It should be noted that, in some embodiments, the compounds described herein can contain one or more chiral centers. These can include racemic mixtures, diastereomers, enantiomers, and mixtures containing one or more stereoisomer. Further, the disclosed can encompass racemic forms of the compounds in addition to individual stereoisomers, as well as mixtures containing any of these.

The synthetic processes discussed herein and their accompanying drawings are prophetic examples, and are not limiting; they can vary in reaction conditions, components, methods, etc. In addition, the reaction conditions can optionally be changed over the course of a process. Further, in some embodiments, processes can be added or omitted while still remaining within the scope of the disclosure, as will be understood by a person of ordinary skill in the art.

Figure 1:
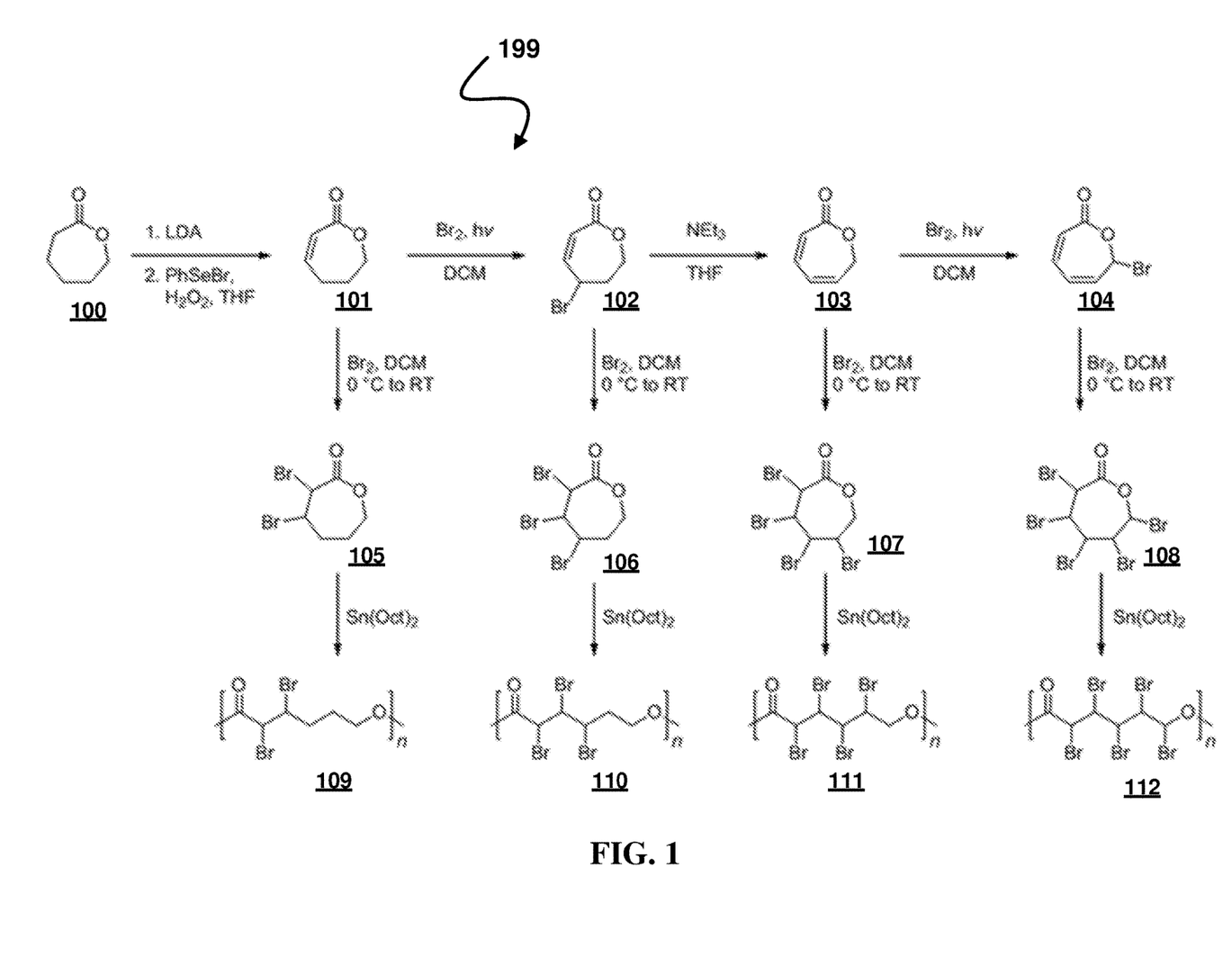
FIG. 1 is an example synthesis diagram representing a synthesis of halogenated PCL flame retardants.

FIG. 1 illustrates an example synthesis 199 of halogenated PCL flame retardants. Starting from caprolactone (CL) 100, an enolate is generated using lithium diisopropylamine (LDA) in a solution of phenylselenyl bromide (PhSeBr), hydrogen peroxide ($H_2O_2$), and tetrahydrofuran (THF), which then undergoes selenoxide elimination to give α,β-unsaturated CL 101. Radical bromination alpha to the unsaturation of CL 101 gives bromo-CL 102. The elimination of the bromine of 102 via the use of a hindered base gives di-unsaturated CL 103. A second radical bromination step results in CL 104 with two unsaturations and a bromide. Each of the unsaturations in CLs 101, 102, 103, and 104 are reacted with bromine to give 2,3-dibromo-CL 105, 2,3,4-tribromo-CL 106, 2,3,4,5-tetrabromo-CL 107, and 2,3,4,5,6-pentabromo-CL 108. These polybromo-CLs, 105-108, which can also be represented by Formula A, are then polymerized using catalytic tin(II) octanoate to give the brominated PCLs 109-112, respectively. The brominated CLs are also polymerized with unfunctionalized CL to give variable control over the bromine content and physical/thermal properties of the polymer. In some embodiments, the brominated CLs 105-108 are alternatively replaced with a compound represented by the Formula A to yield a corresponding polymer represented by n block from Formula 2. In some embodiments, polybromo-CL's 105-108 can be mixed with varying ratios of caprolactone 100 to give a final polymer with varying ratios of m to n block (see Formula 2).

Figure 2:
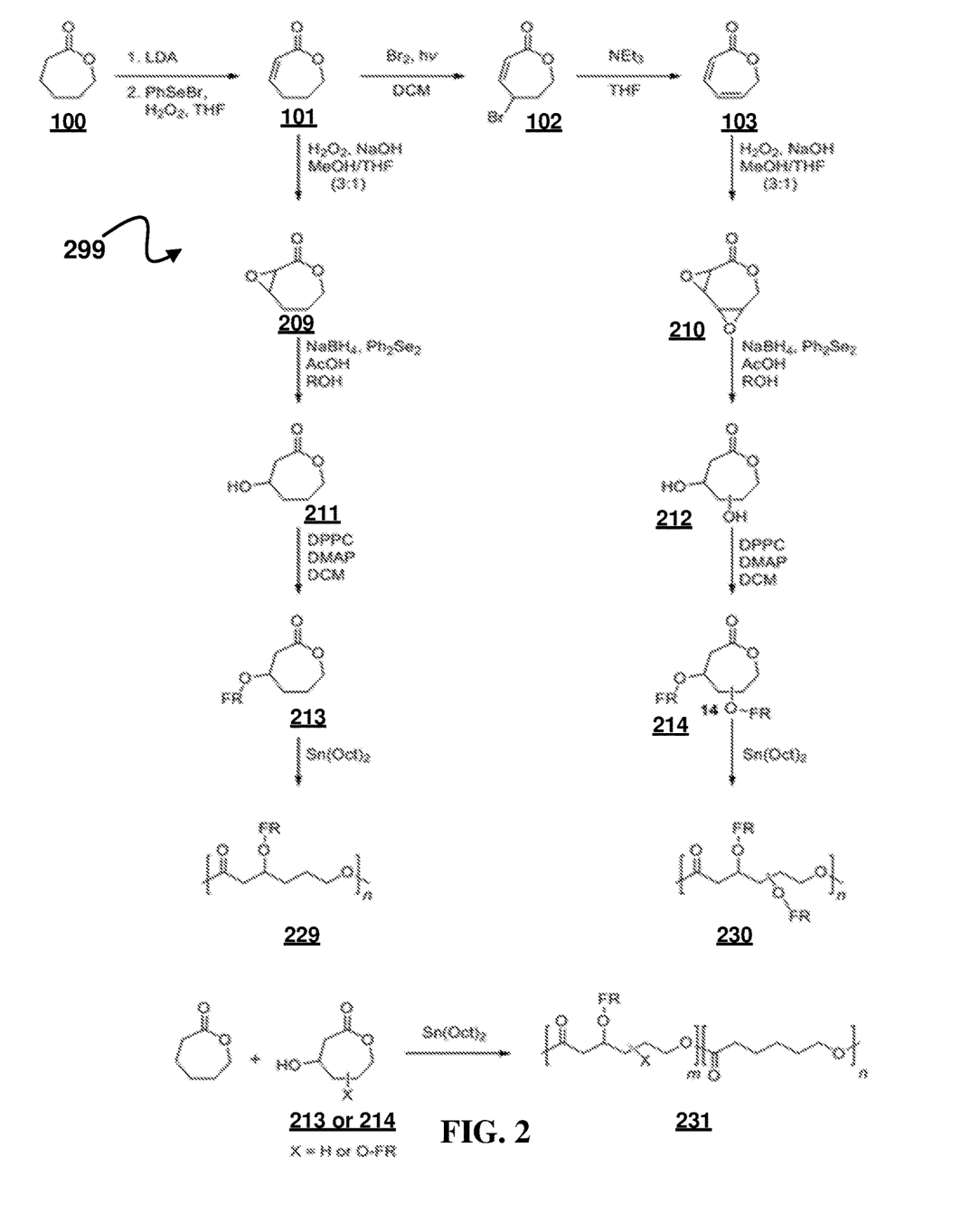
FIG. 2 is an example synthesis diagram representing a synthesis of non-halogenated PCL flame retardants.

FIG. 2 illustrates an example synthesis 299 of non-halogenated PCL flame retardants proceeding through an epoxide (oxirane) intermediate. Staring from caprolactone (CL) 100, CL molecules 101 and 103 are synthesized as described above. 2-oxiranyl-CL 209 and 2,5-dioxiranyl-CL 210 and synthesized from CLs 101 and 103, respectively, from hydrogen peroxide ($H_2O_2$). These epoxides rings are then opened via a reductive ring-opening reaction using sodium borohydride ($NaBH_4$) and phenyl diselenide ($Ph_2Se_2$) to give 3-hydroxyCL 211 and either 3,4- or 3,5-dihydroxyCL 212 (the reaction conditions may give a mixture of stereochemistry for the second epoxide ring-opening). The hydroxyl groups are then functionalized with either phosphoryl or phosphonyl groups via a reaction with either diphenylphosphoryl chloride or diphenylphosphinic chloride (both abbreviated DPPC) with catalytic dimethylaminopyridine (DMAP) to give 213 and 214. The phosphoryl or phosphonyl groups are abbreviate as "FR." The non-halogenated flame retardant-functionalized CLs are then polymerized using catalytic tin(II) octanoate to give the flame retardant PCLs 229 and 230. The non-halogenated FR-functionalized CLs are also polymerized with unfunctionalized CL (100) to give polymer 231. In some embodiments, the non-halogenated FR-functionalized CLs 213 and 214 are alternatively replaced with a compound represented by the Formula A to yield a corresponding polymer represented by n block in Formula 2. The ratio of 213 and/or 214 monomers to 100 monomer gives the ratio of m block to n block in the final polymer, respectively. This can allow for variable control over the flame retardancy and physical/thermal properties of the polymer.

Figure 3:
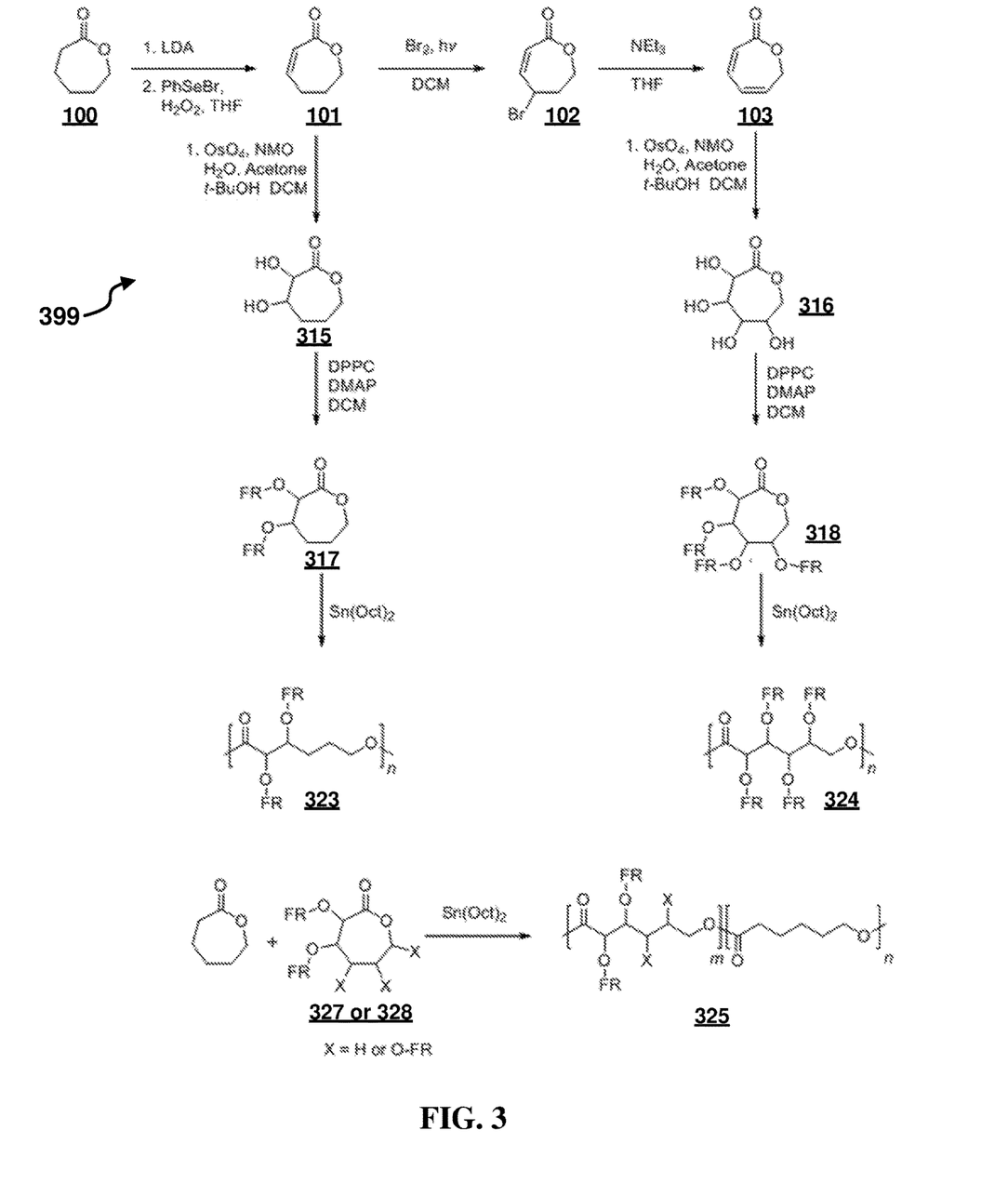
FIG. 3 is an example synthesis diagram representing a synthesis of non-halogenated PCL flame retardants.

FIG. 3 illustrates an example synthesis 399 of non-halogenated PCL flame retardants proceeding through a diol intermediate. CL molecules 101 and 103 are synthesized as described above from caprolactone 100. 2,3-hydroxyl-CL 315 and 2,3,4,5-hydroxyl-CL 316 and synthesized from CLs 1 and 3, respectively, via an Upjohn dihydroxylation reaction involving catalytic osmium tetroxide. The hydroxyl groups are then functionalized with either phosphoryl or phosphonyl groups via a reaction with either diphenylphosphoryl chloride or diphenylphosphinic chloride (both abbreviated DPPC) with catalytic dimethylaminopyridine (DMAP) to give molecules 317 and 318. The phosphoryl or phosphonyl groups are abbreviate as "FR." The non-halogenated flame retardant-functionalized CLs are then polymerized using catalytic tin(II) octanoate to give the flame retardant PCLs 323 and 324. The non-halogenated FR-functionalized CLs 317 and 318 are also polymerized with unfunctionalized CL (100) to give polymer 325. In some embodiments, the non-halogenated FR-functionalized CLs 317 and 318 are alternatively replaced with a compound represented by the Formula A to yield a corresponding polymer represented by Formula 2. These copolymers can allow for variable control over the flame retardancy and physical/thermal properties of the polymer depending on the ratio of unfunctionalized to functionalized CL that is used to yield polymer 325 (also alternatively represented by Formula 2). The ratio of 327 and/or 328 monomers to 100 monomer gives the ratio of m block to n block in the final polymer, respectively.

EXAMPLES

The following are examples of some methods that can be used to prepare and use the compounds described herein.

Example 1

Synthesis of Unsaturated CL 101 n-Butyllithium (1 equivalent) is added dropwise to anhydrous THF and diisopropylamine (1.2 equiv.) in dry THF under nitrogen at −78° C. for 15 minutes. epsilon-Caprolactone (1 equiv.) in dry THF is added dropwise, and the solution stirred at −78° C. for 15 min. Phenylselenyl bromide (1 equiv.) in dry THF is added rapidly between −78 and −60° C., and the solution stirred at −78° C. for 15 min. Water (20 mL) is added and the THF is evaporated in vacuo. The yellow residue is extracted with diethyl ether (4×). The combined organic solvents are washed with water (4×), dried (MgSO$_4$), filtered, and evaporated in vacuo. The residue in ether is kept at −20° C. overnight to give the phenylselenyl lactone (14.1 g) as crystals. The mother liquors are chromatographed on silica gel, eluting with dichloromethane to give more phenylselenyl lactone $R_f$=0.54.

Reaction arrow 1, Step 2: Hydrogen peroxide (30%, 1.3 equiv.) is added dropwise with stirring to the phenylselenyl lactone (1 equiv.) in THF at 25° C. After the addition is completed, the temperature is kept between 30-33° C. for 2.5 hr. The resulting yellow solution is evaporated in vacuo and the residue is chromatographed on silica gel, eluting with ether-light petroleum (boiling point (bp): 30-40° C.) (1:1) to give the lactone product 101 as a yellow oil, $R_f$=0.19, which is further purified by distillation to give a colorless liquid, bp 68-69° C./0.1 mm Hg. See also FIG. 1.

Example 2

Synthesis of 315 and 316

To a stirred solution of "caprolactone-diene" 103 (1 equiv.) in a solution of acetone/water (8:1) may be added (2 equiv.) of N-morpholine oxide (NMO) and a 2.5% solution of OsO$_4$ in tert-butanol (5 mol % of OsO$_4$) and the mixture may be stirred overnight at room temperature. The reaction may be quenched with a saturated solution of Na$_2$S$_2$O$_3$, and may be stirred for one hour and transferred in a separation funnel. The aqueous layer may be extracted with ethyl acetate, the combined organic layers dried over Na$_2$SO$_4$ and the solvent removed under reduced pressure. The crude may be used without purification or residue may be purified by recrystallization or column chromatography. This procedure can also be used in the synthesis of 315 from 101, but the amount of NMO may be halved to 1 equiv. and the amount of OsO$_4$ may be reduced to 2.5 mol %. See also FIG. 3.

Example 3

Synthesis of 318

To a solution of "tetrahydroxycaprolactone" 316 (1 equiv.) and diphenyl chlorophosphate (>4 equiv.) in anhydrous DCM or THF at 0° C., is added a solution of triethylamine and/or DMAP (>4 equiv.) in anhydrous DCM or THF, dropwise. The reaction may be heated to reflux and stirred for up to 24 hours. The reaction may be poured into a saturated solution of ammonium chloride, and may be stirred for one hour and transferred in a separation funnel. The aqueous layer may be extracted with ethyl acetate, the combined organic layers dried over Na$_2$SO$_4$ and the solvent removed under reduced pressure. The crude 318 may be used without purification or residue may be purified by recrystallization or column chromatography. See also FIG. 3.

Example 3

Homopolymer Polymerization

"Phosphorylated caprolactone" or and a catalysts such as tin (II) octanoate (0.1-1 mol %) may be added to a reaction vessel, which may contain a solvent such as DCM. After a period of up to 24 hours, the melt or solution may be added directly to hexanes or methanol, dropwise or all in one portion, to precipitate the polymer, which may be collected by filtration, and dried in a vacuum oven at >60° C. until complete removal of volatiles (determined by thermogravimetric analysis).

Example 4

Heteropolymer Polymerization

"Phosphorylated caprolactone" or brominated caprolactone, unsubstituted caprolactone, and a catalysts such as tin (II) octanoate (0.1-1 mol %) can be added to a reaction vessel, which can contain a solvent such as DCM. After a period of up to 24 hours, the melt or solution can be added directly to hexanes or methanol, dropwise or all in one portion, to precipitate the polymer, which can be collected by filtration, and dried in a vacuum oven at >60° C. until complete removal of volatiles (determined by thermogravimetric analysis).

Example 5

Synthesis of 102

To a stirred anhydrous solution of "caprolactone" (compound 101) in a solution of either anhydrous DCM or benzene, may be added bromine dropwise. The solution may include a free radical initiator such as AIBN or benzoyl peroxide. The solution may be heated to reflux and/or placed under UV radiation (approx. 254 nm). Upon completion, reaction may be filtered, or quenched with a sodium thiosulfate solution and the layers separated. The organic layer may be rinsed with water and brine, and may be dried over MgSO$_4$. The solvent may be removed in vacuo and the residue may be purified by recrystallization or column chromatography.

Example 6

Synthesis of 104

To a stirred anhydrous solution of "caprolactone" (compound 103) in a solution of either anhydrous DCM or benzene, may be added bromine dropwise. The solution may include a free radical initiator such as AIBN or benzoyl peroxide. The solution may be heated to reflux and/or placed under UV radiation (approx. 254 nm). Upon completion, reaction may be filtered, or quenched with a sodium thiosulfate solution and the layers separated. The organic layer may be rinsed with water and brine, and may be dried over $MgSO_4$. The solvent may be removed in vacuo and the residue may be purified by recrystallization or column chromatography.

Example 7

Synthesis of 103

To a stirred anhydrous solution of "bromocaprolactone" 102 in a solution of either anhydrous DCM or THF, may be added a solution of triethylamine in the same solvent, dropwise. The solution may be heated to reflux. Upon completion, reaction may be quenched with a sodium thiosulfate solution, and the layers separated. The organic layer may be rinsed with water and brine, and may be dried over $MgSO_4$. The solvent may be removed in vacuo and the residue may be purified by recrystallization or column chromatography. See FIG. 1.

Example 8

Synthesis of 105-108

To a stirred anhydrous solution of "caprolactone" (compounds 101-104) in a solution of anhydrous DCM, may be added bromine dropwise (>1 equiv. per alkene). The solution may be warmed to room temperature and/or stirred for 1-8 hours. Upon completion, reaction may be filtered, or quenched with a sodium thiosulfate solution and the layers separated. The organic layer may be rinsed with water and brine, and may be dried over $MgSO_4$. The solvent may be removed in vacuo and the residue may be purified by recrystallization or column chromatography (e.g. as seen in FIG. 1, using compound 101 in this reaction yields compound 105, using compound 102 yields compound 106, etc.).

Example 9

Synthesis of 209

To a solution of compound 101 (1.0 equiv.) in MeOH-THF (3:1, 400 mL) may be added a solution of aqueous $H_2O_2$ (>10 equiv., 35% w/w) and 6M aqueous NaOH (>1.0 equiv.) at 0° C. After being stirred at the same temperature for 2 hours, to the reaction mixture may be added $H_2O$, ether and a solution of 2M aqueous HCl. The organic phase may be separated, and the aqueous phase may be extracted with ether (2×). The combined organic extracts may be washed with brine, dried over anhydrous $Na_2SO_4$ and concentrated in vacuo. The residue may be purified by silica gel column chromatography.

Example 10

Synthesis of 210

To a solution of compound 103 (2.0 equiv.) in MeOH-THF (3:1, 400 mL) may be added a solution of aqueous $H_2O_2$ (>20 equiv., 35% w/w) and 6M aqueous NaOH (>2.0 equiv.) at 0° C. After being stirred at the same temperature for 2 hours, to the reaction mixture may be added $H_2O$, ether and a solution of 2M aqueous HCl. The organic phase may be separated, and the aqueous phase may be extracted with ether (2×). The combined organic extracts may be washed with brine, dried over anhydrous $Na_2SO_4$ and concentrated in vacuo. The residue may be purified by silica gel column chromatography.

Example 11

Synthesis of 211

To a stirred solution of diphenyl diselenide (1.33 equiv.) in isopropanol may be added $NaBH_4$ (2.66 equiv.) at ambient temperature. After a few minutes acetic acid may be added at the same temperature. After 5 minutes, the mixture may be cooled to 0° C., and a solution of the epoxy lactone (1.0 equiv.) isopropanol may be added dropwise to the mixture. Stirring may be continued for 30 min at the same temperature. The mixture is diluted with ethyl acetate, and the organic layer may be washed with brine and dried with $MgSO_4$. After evaporation of the solvent under reduced pressure, the residue may be purified by silica gel column chromatography.

Example 12

Synthesis of 212

To a stirred solution of diphenyl diselenide (2.66 equiv.) in isopropanol may be added $NaBH_4$ (5.32 equiv.) at ambient temperature. After a few minutes acetic acid may be added at the same temperature. After 5 minutes, the mixture may be cooled to 0° C., and a solution of the epoxy lactone (2.0 equiv.) isopropanol may be added dropwise to the mixture. Stirring may be continued for 30 min at the same temperature. The mixture is diluted with ethyl acetate, and the organic layer may be washed with brine and dried with $MgSO_4$. After evaporation of the solvent under reduced pressure, the residue may be purified by silica gel column chromatography.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A process of forming a flame retardant polycaprolactone, the process comprising:
   hydroxylating caprolactone;
   chemically reacting the hydroxylated caprolactone with a phosphorus-based compound to form a caprolactone monomer having phosphorus-based moieties; and
   polymerizing a mixture that includes at least the caprolactone monomer to form the flame retardant polycaprolactone.

2. The process of claim 1, wherein at least one of the phosphorus-based moieties is a phosphoryl moiety.

3. The process of claim 1, wherein at least one of the phosphorus-based moieties is a phosphonyl moiety.

4. The process of claim 1, wherein the flame retardant caprolactone monomer has one, two, three, four, or five of the phosphorus-based moieties.

5. The process of claim 1, wherein the mixture includes additional caprolactone.

6. The process of claim 5, wherein the flame retardant polycaprolactone is a copolymer of the flame retardant caprolactone monomer and the additional caprolactone.

* * * * *